(12) United States Patent
Landgrebe et al.

(10) Patent No.: US 9,358,071 B2
(45) Date of Patent: Jun. 7, 2016

(54) STERILIZATION WRAP SYSTEM AND METHODS OF USE

(71) Applicant: 3M INNOVATIVE PROPERTIES COMPANY, St. Paul, MN (US)

(72) Inventors: Kevin D. Landgrebe, Woodbury, MN (US); Susan K. Reed, North Oaks, MN (US); Heather M. Webb, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/506,944

(22) Filed: Oct. 6, 2014

(65) Prior Publication Data

US 2015/0021212 A1  Jan. 22, 2015

Related U.S. Application Data

(62) Division of application No. 13/334,730, filed on Dec. 22, 2011, now Pat. No. 8,852,502.

(60) Provisional application No. 61/428,703, filed on Dec. 30, 2010.

(51) Int. Cl.
| | |
|---|---|
| *A61M 1/00* | (2006.01) |
| *B65B 51/10* | (2006.01) |
| *F26B 21/06* | (2006.01) |
| *C12Q 1/68* | (2006.01) |
| *A61B 19/02* | (2006.01) |
| *A61L 2/26* | (2006.01) |
| *A61B 19/08* | (2006.01) |

(52) U.S. Cl.
CPC .............. *A61B 19/026* (2013.01); *A61L 2/26* (2013.01); *A61B 19/08* (2013.01); *A61B 2019/0201* (2013.01); *A61L 2202/181* (2013.01)

(58) Field of Classification Search
CPC ............. A61L 2/07; A61L 2/00; A61L 17/00; G09F 3/10; B32B 3/00
USPC ....... 604/317; 53/477; 34/82, 587; 96/7, 136, 96/147, 223; 220/495.01, 23.83, 500, 371; 422/1, 26–28, 32, 50, 19, 119; 435/6.1, 435/23
See application file for complete search history.

(56) References Cited

U.S. PATENT DOCUMENTS

| 4,041,203 A | 8/1977 | Brock et al. ................... 428/157 |
| 5,635,134 A | 6/1997 | Bourne et al. ................... 422/26 |
| 5,688,476 A | 11/1997 | Bourne et al. ................. 422/294 |

(Continued)

FOREIGN PATENT DOCUMENTS

| GB | 2 292 325 | 2/1996 | .............. B65B 11/48 |
| JP | 2005-132495 | 5/2005 | |
| WO | WO 2010/042847 | 4/2010 | .............. B65B 61/14 |

OTHER PUBLICATIONS

Seavey, R.; "Education and Training—It's a Wrap! Sterilization Packaging Systems, Preparation and Loading for Steam Sterilization"; Managing Infection Control; 2006; pp. 78-97.

*Primary Examiner* — Monzer R Chorbaji (57) ABSTRACT

A method of sterilizing an article is provided. The method includes providing sterilization wrap system with which to wrap the article to be sterilized. The sterilization wrap system comprises a plurality of wrap units configured in a stack, at least one wrap unit in the stack being detachably attached to at least one other wrap unit in the stack.

11 Claims, 8 Drawing Sheets

(56) References Cited

U.S. PATENT DOCUMENTS

| | | | |
|---|---|---|---|
| 6,406,764 B2 | 6/2002 | Bayer | 428/35 |
| 6,517,916 B1 | 2/2003 | Bayer et al. | 428/34 |
| 6,630,104 B1 | 10/2003 | Bayer | 422/1 |
| 6,793,879 B2 | 9/2004 | Bayer et al. | 422/1 |
| 7,361,317 B2 | 4/2008 | Bourne et al. | 422/292 |
| 7,560,082 B2 | 7/2009 | Stecklein et al. | 422/294 |
| 2002/0124947 A1 | 9/2002 | Kim | 156/247 |
| 2004/0261373 A1* | 12/2004 | Bowen | A61L 2/26 53/477 |
| 2005/0079093 A1 | 4/2005 | Cannady et al. | 422/1 |
| 2005/0092636 A1 | 5/2005 | Su-Syin | |
| 2006/0067855 A1 | 3/2006 | Mathis et al. | 422/28 |
| 2006/0104856 A1 | 5/2006 | Farrell et al. | 422/1 |
| 2006/0153759 A1 | 7/2006 | Bayer et al. | 422/292 |
| 2007/0128094 A1 | 6/2007 | Paris-Jolly et al. | 422/292 |
| 2009/0257913 A1 | 10/2009 | Stecklein et al. | 422/28 |
| 2010/0158751 A1 | 6/2010 | Friderich et al. | 422/27 |

* cited by examiner

STERILIZATION WRAP SYSTEM AND METHODS OF USE

CROSS REFERENCE TO RELATED APPLICATIONS

This application is a divisional of U.S. Ser. No. 13/334,730, filed Dec. 22, 2011 (now U.S. Pat. No. 8,852,502), which claims the benefit of U.S. Provisional Patent Application No. 61/428,703, filed Dec. 30, 2010, which is incorporated herein by reference in their entirety.

BACKGROUND

Reusable instruments that require sterilization are reprocessed in most hospitals. Reprocessing involves cleaning and packaging instruments, sterilizing them, and storing them until they are needed by the operating rooms or other departments in the hospital.

When preparing instruments for sterilization, the instruments are typically placed into stainless steel instrument trays and the entire tray is wrapped using sterilization wrap. A sterilization wrap typically is permeable to a sterilant (e.g., steam, ethylene oxide, etc.) so that the enclosed instruments are properly sterilized when exposed to a sterilization process. Furthermore, the sterilization wrap typically maintains sterility of the enclosed articles after reprocessing by presenting a barrier to entry of microorganisms. One of the most common ways for the sterility of wrapped instruments to become compromised is by a tear or hole in the sterilization wrap.

In order to promote and maintain the sterility of the packaged contents, the Association of Operating Room Nurses (AORN) developed recommended practices for the wrapping and handling of in-hospital processed packages. AORN recommends double wrapping of in-hospital processed packages. In double wrapping, two layers of sterilization wrap are either simultaneously or sequentially applied. Alternatively, a so-called single-step sterilization wrap that has two layers of sterilization wrap connected one to the other is used. While the implementation of doubly-wrapped packages has been shown to reduce compromised wrapped items due to holes or tears, there are still many instances of at least one of the layers of wrap in a double-wrapped package having a tear or hole after processing and handling.

There remains a need for a simple, versatile sterilization wrap system for use with the wide variety of objects that are wrapped and sterilized in a hospital.

SUMMARY

In general, the invention is directed to a versatile sterilization wrap system that can be used to dispense one or more wrap units. Methods of use of the sterilization wrap system are also disclosed.

Each wrap unit comprises a substantially planar material with a periphery, an upper surface, and a lower surface. Individual wrap units of the sterilization wrap system are detachably attached via attachment means to at least one or more other wrap units. The wrap units in the sterilization wrap system are disposed in a stack comprising a plurality of wrap units. In certain some embodiments, at least a portion of the periphery of two or more detachably attached wrap units is aligned. Advantageously, this feature permits dispensing two or more aligned wrap units from the stack. Furthermore, the attachment means can maintain alignment of two or more wrap units before or during an article-wrapping process.

In one aspect, the present disclosure provides a method of sterilizing an article. The method can comprise providing an article and a sterilization wrap system that includes a plurality of wrap units configured in a stack, each wrap unit comprising an upper surface and a lower surface. At least one wrap unit can be detachably attached via an attachment means to at least one other wrap unit in the stack. The method further can comprise detaching a first wrap unit from the stack, wrapping the article with the first wrap unit, and exposing the wrapped article to sterilization conditions.

In another aspect, the present disclosure provides a method of sterilizing an article. The method can comprise providing an article and a sterilization wrap system that includes a plurality of wrap units configured in a stack, each wrap unit comprising an upper surface and a lower surface. At least one wrap unit can be detachably attached via an attachment means to at least one other wrap unit in the stack. The method further can comprise placing the article onto a first wrap unit, wherein the first wrap unit is a topmost wrap unit of the stack; wrapping the article with the first wrap unit; detaching the first wrap unit from the stack; and exposing the wrapped article to sterilization conditions.

In any embodiment of the above methods, detaching the first wrap unit can further comprise detaching the first wrap unit with a second wrap unit attached thereto, wherein wrapping the article can comprise wrapping the article with the first and second wrap units. In some embodiments, wrapping the article can comprise simultaneously wrapping the article with the first and second wrap units.

In yet another aspect, the present disclosure provides a method of sterilizing an article. The method can comprise providing an article and a sterilization wrap system that includes a plurality of wrap units configured in a stack, each wrap unit comprising an upper surface and a lower surface. At least a first wrap unit is detachably attached via an attachment means to a second wrap unit in the stack. The method further can comprise placing the article between the first and second wrap units, wrapping the article with the first and second wrap units; detaching the first and second wrap units from the stack, and exposing the wrapped article to sterilization conditions.

In any of the above embodiments of the method, wrapping the article can comprise securing a portion of one wrap unit to another portion of the same wrap unit. In any of the above embodiments of the method, wrapping the article can comprise securing a portion of one wrap unit to a portion of another wrap unit. In any of the above embodiments of the method, securing a portion can comprise securing the portion via the attachment means.

In any of the above embodiments, the method further can comprise securing a portion of one sheet to another portion of the same sheet or securing a portion of one sheet to a portion of another sheet via a fastener. In some embodiments, the fastener further can comprise a visual sterilization indicator.

In yet another aspect, the present disclosure provides a sterilization wrap system. The sterilization wrap system can comprise a plurality of wrap units configured in a stack. Each wrap unit can comprise sheet material that is substantially permeable to vapor-phase sterilants and has filtration properties sufficient to prevent the passage of pathogenic organisms therethrough. At least one wrap unit in the stack can be detachably attached via an attachment means to another wrap unit in the stack. In some embodiments of the sterilization wrap system, the sheet material can comprise a nonwoven material or a medical grade paper. In any of the above embodiments, the nonwoven material can comprise cellulose, rayon, a thermoplastic polymer, a derivative of any of the foregoing materials, or a combination of any two or more of the foregoing materials. In any one of the above embodiments, the thermoplastic polymer can comprise a polyolefin polymer, a polyester polymer, or a polyamide polymer. In any of the above embodiments of the sterilization wrap system, the sheet material can be made using a process selected from the group consisting of an air laying process, a wet-laid process, a hydroentangling process, spunbonding, meltblowing, staple fiber carding and bonding, and solution spinning. In any of the above embodiments of the sterilization wrap system, the sterilization wrap can consist essentially of a three-ply laminate of spunbond polypropylene-meltblown polypropylene-spunbond polypropylene. In any of the above embodiments of the sterilization wrap system, each wrap unit in the stack can be detachably attached to a wrap, if present, positioned immediately above it in the stack. In any of the above embodiments of the sterilization wrap system, the attachment means can be selected from the group consisting of comprises an adhesive means, a mechanical means, or a surface-modification means. In any of the above embodiments of the sterilization wrap system, the attachment means can be selected from the group consisting of comprises a wax. In any of the above embodiments, the attachment means can be positioned on a major surface of a first wrap unit and the attachment means can be detachably attached to a major surface of a second wrap unit. In any of the above embodiments, the attachment means coupling a first wrap unit to a second wrap unit can be positioned along at least a portion of an edge of each of the first and second wrap units.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a wrap unit can be interpreted to mean "one or more" wrap units.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and in the description below. Other features, objects and advantages will become apparent from the description and drawings, and from the claims.

DETAILED DESCRIPTION

The invention is directed to a versatile sterilization wrap system that can be used to dispense one or more wrap units. The wrap units are disposed in a stack wherein at least one wrap unit is detachably attached to at least one adjacent wrap unit. The wrap units can be dispensed from the stack before wrapping an article or after wrapping the article. The inventive system permits the operator sequentially to dispense individual wrap units for wrapping an article with one, two, three, or more layers (e.g., wrap units). Alternatively, the system permits the operator simultaneously to dispense two, three, or more layers (e.g., wrap units) that, optionally, are aligned and detachably attached to one another.

The present disclosure provides a method of sterilizing an article. All embodiments of the method include providing a sterilization wrap system comprising a stack of wrap units as described herein. Furthermore all embodiments of the method include wrapping an article to be sterilized and exposing the wrapped article to sterilization conditions. Wrapping the article can be done according to conventional methods known in the art. By way of example, methods of wrapping an article to be sterilized are shown (FIGS. 5-6) and described in a paper written by Rose Seavey (Sterilization Packaging Systems, Preparation and Loading for Steam Sterilization, Managing Infection Control, December 2006, pages 78-97), which is incorporated herein by reference in its entirety. Exposing an article to sterilization conditions can include, exposing the article to a process that uses one or more of the following: dry heat, moist heat, steam, ethylene oxide, a peroxide compound, ozone, ionizing radiation, for example.

Figure 1:
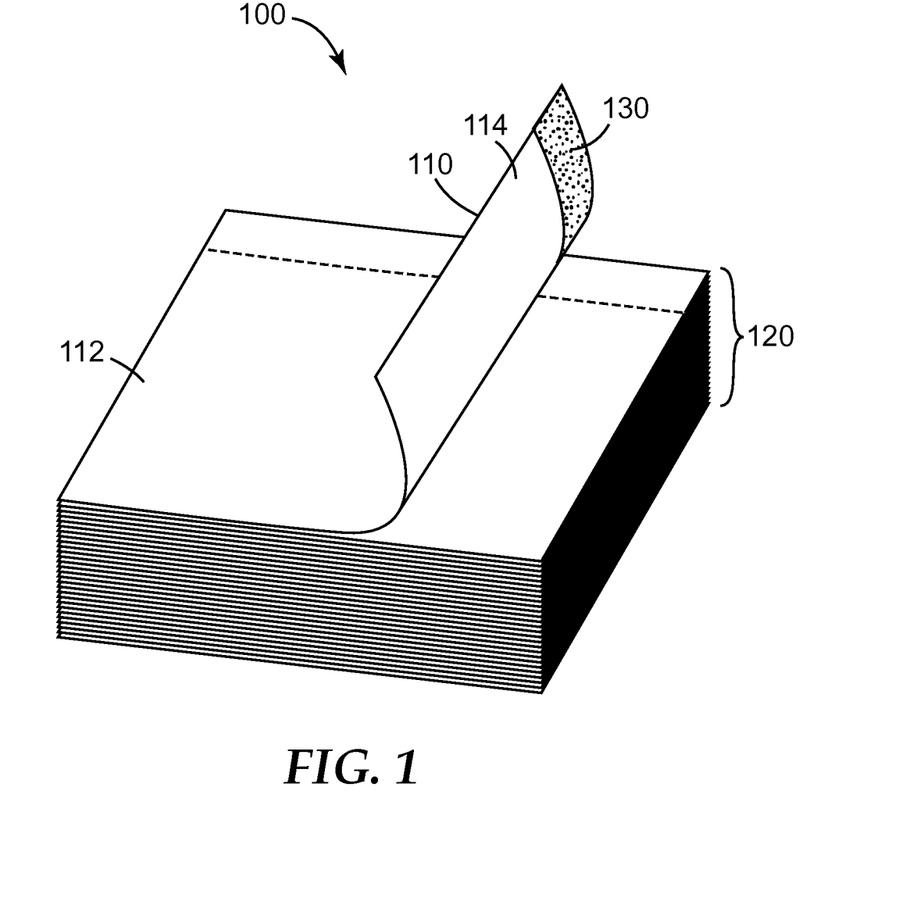
FIG. 1 is a top perspective view of one embodiment of a sterilization wrap system according to the present disclosure block diagram of one embodiment of a method for sterilizing an article according to the present disclosure.

FIG. 1 shows a top perspective view of one embodiment of a sterilization wrap system 100 according to the present disclosure. The system 100 comprises a plurality of wrap units 110. The wrap units 110 comprise sheet material, each wrap unit having an upper surface 112 and a lower surface 114. The wrap units 100 are disposed in a stack 120 comprising a plurality of wrap units 110.

A "wrap unit", as used herein, refers to a single, substantially-planar sheet used to wrap an article to be sterilized. The sheet material used to fabricate the wrap units can be any sheet material that is resistant to tearing when wrapping articles to be sterilized, that is substantially permeable to vapor sterilants (e.g., steam, ethylene oxide, peroxide, and/or ozone), and that has filtration properties sufficient to prevent the passage of pathogenic microorganisms therethrough. In some embodiments, the sheet material comprises a nonwoven material. The sheet material can be fabricated from a variety of materials including, but not limited to, medical grade paper, rayon, polyolefin, polyester, polylactic acid, or a combination of any two or more of the foregoing materials. The sheet material can be made using a variety of processes including, but not limited to, air laying processes, wet-laid processes, a meltblowing processes, staple fiber carding and bonding processes, and a solution spinning processes. In some embodiments, a wrap unit can consist of a three-ply laminate of spunbond polypropylene-meltblown polypropylene-spunbond polypropylene (i.e., an "SMS" tri-laminate).

In some embodiments, each of the wrap units in the stack is substantially identical to the other wrap units in the stack. In some embodiments, the stack can comprise wrap units having different compositions and/or properties (e.g., tensile strength, moisture resistance). In some embodiments, the stack can comprise alternating wrap units of two or more different compositions, optionally configured in a repeating pattern.

The wrap units can be fabricated in a variety of shapes and/or sizes to wrap various size items and trays. In some embodiments, the wrap units can be square-shaped having sides with lengths of approximately 18 inches (46 cm), 24 inches (61 cm), 30 inches (76 cm), 36 inches (91 cm), 40 inches (102 cm), 45 inches (114 cm), 48 inches (122 cm), and 54 inches (137 cm). In some embodiments, the wrap units can be rectangular-shaped.

Referring back to FIG. 1, at least two wrap units 110 in the stack 120 are detachably attached via an attachment means 130. In some embodiments, each wrap unit 110 in the stack 120 is detachably attached to at least one other, preferably adjacent, wrap unit 110. In some embodiments, each wrap unit 110 is detachably attached to adjacent wrap units above it and below it, if such wrap units are present, in the stack.

Wrap units 110 in the stack 120 can be detachably attached via a variety of attachment means 130. Non-limiting examples of attachment means 130 include adhesive means (e.g., an adhesive layer, adhesive tape, wax), mechanical means (e.g., a stitch, a staple, a heat bond, an ultrasonic weld, hook-and-loop elements, interlocking geometrically-shaped elements), and surface modification (e.g., complementary electrostatic charges). In general, the attachment means should not compromise the integrity of a wrap unit during the manufacture or use of the sterilization wrap system.

In some embodiments, the attachment means comprises a wax (e.g., a paraffin wax). Preferably, the wax has a melting point higher than 37° C. More preferably, the wax has a melting point higher than 40° C. More preferably, the wax has a melting point higher than 42° C. In one embodiment, when attaching two wrap units together, a piece (e.g., a strip) of solid wax can be positioned between adjacent wrap units, the wrap units can be heated briefly to melt the wax, and the wrap units can be cooled to room temperature to solidify the wax, thereby bonding the wrap units together.

The force needed to separate two wrap units joined via an attachment means should be relatively low, thereby permitting a relatively smooth, easy process to separate wrap units from a stack during use. In certain preferred embodiments, the force required to separate detachably attached wrap units is less than about 450 grams. More preferably, the force required to separate detachably attached wrap units is less than about 150 grams. Even more preferably, the force required to separate detachably attached wrap units is less than about 100 grams. In some embodiments, the force required to separate detachably attached wrap units is less than about 50 grams.

In some embodiments, the force required to separate detachably attached wrap units is at least about 1 gram. In some embodiments, the force required to separate detachably attached wrap units is at least about 2 grams. In some embodiments, the force required to separate detachably attached wrap units is at least about 5 grams. In some embodiments, the force required to separate detachably attached wrap units is at least about 7.5 grams. In some embodiments, the force required to separate detachably attached wrap units is at least about 50 grams.

In some embodiments, the force required to separate detachably attached wrap units is between 1 gram and 450 grams, inclusive. In some embodiments, the force required to separate detachably attached wrap units is between 1 gram and 150 grams, inclusive. In some embodiments, the force required to separate detachably attached wrap units is between 1 gram and 100 grams, inclusive. In some embodiments, the force required to separate detachably attached wrap units is between 1 gram and 51 grams, inclusive. In some embodiments, the force required to separate detachably attached wrap units is between 7 grams and 450 grams, inclusive. In some embodiments, the force required to separate detachably attached wrap units is between 7.5 grams and 51 grams, inclusive.

The wrap units may be joined at the extreme periphery of the stack or they may be joined at a distance from the periphery (e.g., at a more central location of a surface of the wrap unit). In one embodiment (not shown), the wrap units may be joined (e.g., by an adhesive or by heat bonding) at the extreme periphery of each wrap unit in the stack, such that the attachment means is essentially coupled to at least a portion of the edge of each wrap unit, rather than being coupled to an upper or lower surface of the wrap unit. Such a joining configuration is common in binding individual pages in a book or a tablet, for example.

When adjacent wrap units 110 joined by an attachment means 130 are separated, as shown in FIG. 1, the certain attachment means 130 (e.g., an adhesive layer, an adhesive tape) generally will remain coupled to one of the wrap units. In some embodiments, when adjacent wrap units 110 joined by an attachment means 130 are separated, the attachment means 130 may remain coupled to the lower surface 114 of one of the wrap units 110, as shown in FIG. 1. In an alternative embodiment (not shown), when adjacent wrap units joined by an attachment means are separated, the attachment means may remain coupled to the lower surface of one of the wrap units. In yet another embodiment (not shown) wherein adjacent wrap units joined by a plurality of attachment means are separated, at least one attachment means may remain coupled to the upper surface of one of the wrap units and at least one attachment means may remain coupled to the lower surface of the adjacent wrap unit.

In some embodiments, at least a portion of the upper surface 112 and/or lower surface 114 of a wrap unit 110 can be adapted such that the attachment means (e.g., an adhesive layer, an adhesive tape) is more or less likely to remain coupled to that portion of the surface when the wrap unit 110 is separated from a wrap unit attached thereto. Such adaptations are known in the art and include, for example, treating the surface to make it smoother to promote better adhesive contact, treating the surface to make it rougher to decrease adhesive contact, chemically treating the surface with a primer to promote greater adhesion, and chemically treating the surface with a release agent to decrease adhesion.

In some embodiments, two wrap units 110 can be detachably attached by a singular attachment means 130 (e.g., a single strip of adhesive tape), such as the singular attachment means 130 extending the length of one edge of the periphery of the wrap unit 110, as shown in FIG. 1. In some embodiments (not shown), the attachment means may extend less than the full length of one edge of the periphery. In some embodiments (not shown), the attachment means may comprise a plurality of attachment means extending along a portion or the full length of at least one edge of the periphery of the wrap units. In some embodiments (not shown), the attachment means can be positioned in the central portion of the wrap unit.

Figure 2A:
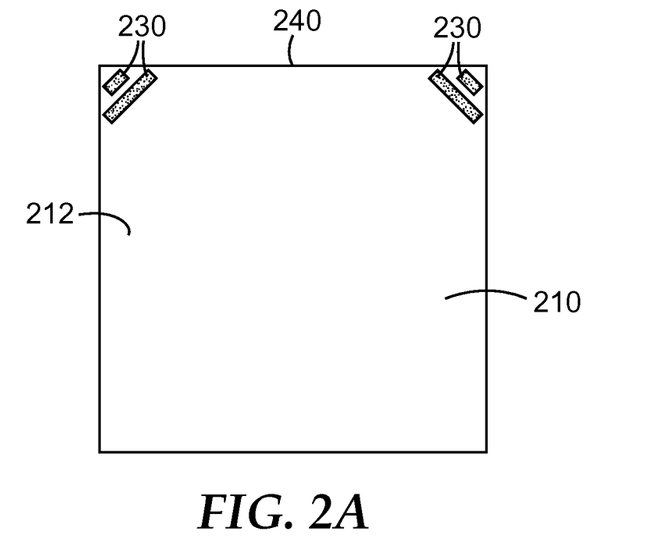
FIG. 2A is a top view of one embodiment of a wrap unit comprising a plurality of attachment means.

FIG. 2A shows a top view of a sterilization wrap unit 210 with a plurality of attachment means 230 attached thereto. The attachment means 230 are positioned on the upper surface 212 at two corners located at opposite ends of a peripheral edge 240 of the wrap unit 210. In an alternative embodiment (not shown) the attachment means can be positioned in one corner of the wrap unit. In an alternative embodiment (not shown), at least one or all of the plurality of attachment means can be positioned on the lower surface of the wrap unit. A plurality of sterilization wrap units 210 shown in FIG. 2A can be combined to form a stack (not shown) similar to the stack illustrated in FIG. 1, for example.

Figure 2B:
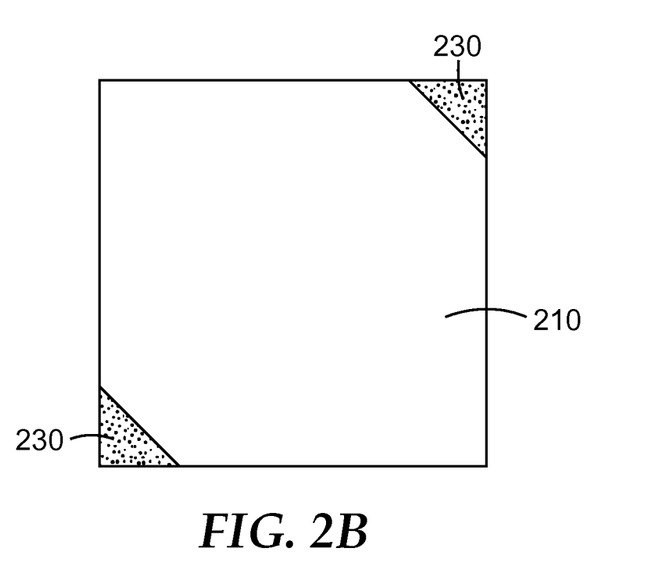
FIG. 2B is a top view of another embodiment of a wrap unit comprising a plurality of attachment means.

FIG. 2B shows a top view of a sterilization wrap unit 210 with a plurality of attachment means 230 attached thereto. The attachment means 230 are positioned on the upper surface 212 at two opposite corners of the wrap unit 210. In an alternative embodiment (not shown), at least one or all of the plurality of attachment means can be positioned on the lower surface of the wrap unit. A plurality of sterilization wrap units 210 shown in FIG. 2B can be combined to form a stack (not shown) similar to the stack illustrated in FIG. 1, for example.

Figure 3:
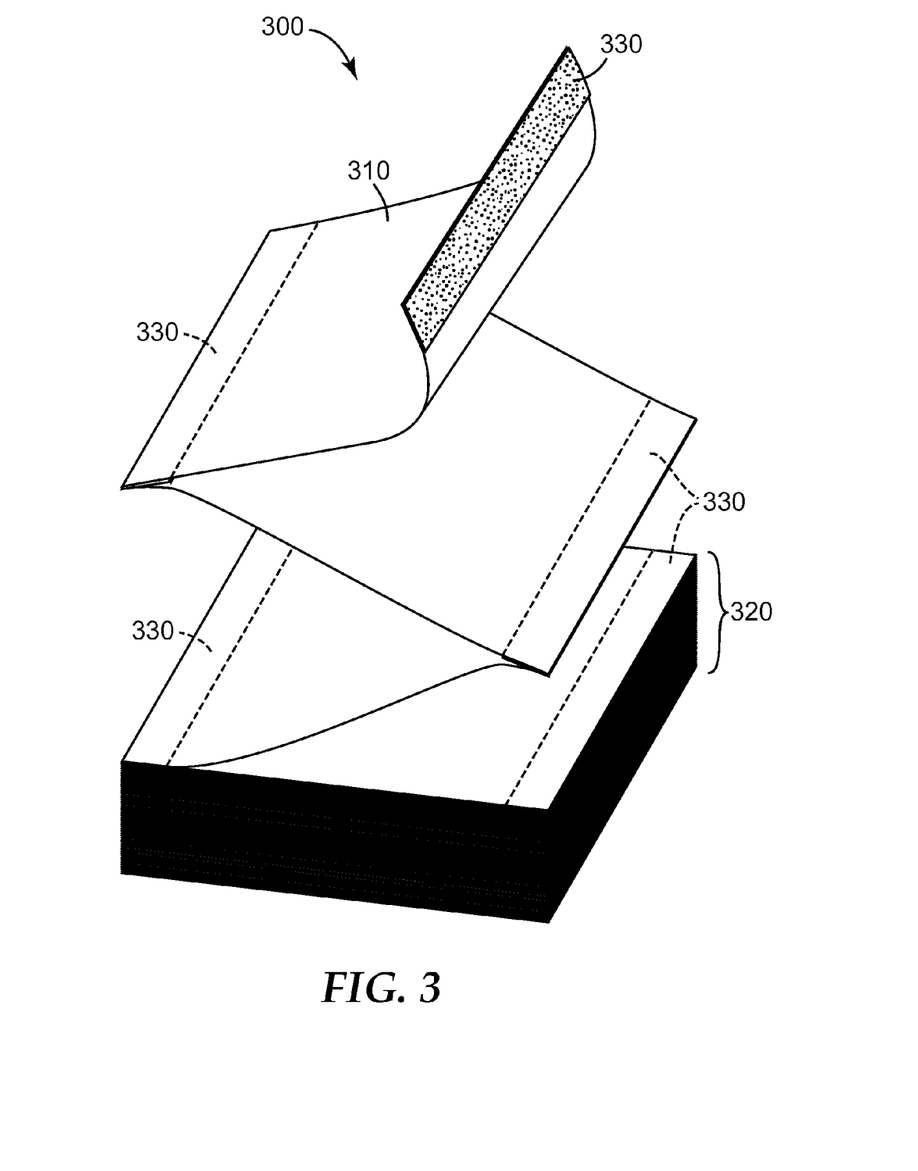
FIG. 3 is a perspective view of another embodiment of a sterilization wrap system.

FIG. 3 shows a perspective view of another embodiment of a sterilization wrap system according to the present disclosure. In the illustrated embodiment, the plurality of wrap units 310 forming the stack 320 are coupled together via attachment means 330 in a Z-fold type configuration (i.e., the attachment means 330 are positioned at opposite edges of the wrap units 310 in each successive layer of the stack 320).

In some embodiments, when using a sterilization wrap system of the present disclosure, an article can be wrapped with one or more wrap units comprising a single layer. In some alternative embodiments, when using a sterilization wrap system according to the present disclosure, and article can be wrapped with two or more layers and/or it can be wrapped with two or more wrap units. In these embodiments, each of the layers and/or wrap units can have its own special characteristics. The main function of an inner layer or wrap unit can be to act as a primary filtration barrier while the primary function of an outer layer or wrap unit can be to provide strength with a secondary function of also providing a barrier to bacteria and other contaminants.

Wrap units can be made from a number of materials. Sterilization wraps are generally characterized as falling into two main classes, reusables and disposables. Reusables are materials which, as the name suggests, can be reused, typically by washing or by some other form of cleaning. Disposables, on the other hand, are usually one-use items that are discarded or recycled after their initial use. Generally, cloth, linen or other woven materials fall into the reusable category while disposables normally include nonwoven materials made from either or both natural and synthetic fibers such as paper, fibrous polymeric nonwovens as well as films that are capable of passing sterilants and retarding transmission of bacteria and other contaminants.

Nonwoven sterilization wraps have become particularly well-liked due to their barrier properties, economics and consistent quality. The nonwoven materials can be made from a variety of processes including, but not limited to, air laying processes, wet laid processes, hydroentangling processes, spunbonding, meltblowing, staple fiber carding and bonding, and solution spinning. The fibers themselves can be made from a variety of both natural and synthetic materials including, but not limited to, cellulose, rayon, polyesters, polyolefins, polyamides, and many other thermoplastic materials. The fibers may be relatively short, staple length fibers, typically less than 3 inches, or longer and substantially more continuous fibers such as are produced by spunbonding and meltblowing processes. Whatever materials are chosen, the resultant wrap must be compatible with the particular sterilization technique being used and must also provide both strength and barrier properties to maintain the sterile nature of the wrapped contents until use.

It has been found that polyolefin-based fibers and their resultant nonwovens are particularly well-suited for the production of sterilization wrap. Polypropylene spunbonded nonwovens such as are produced by Kimberly-Clark Corporation can be used to impart strength characteristics to the sterilization wrap.

A spunbonded, meltblown, spunbonded material is made from three separate layers that are laminated to one another. The method of making these layers is known and described in U.S. Pat. No. 4,041,203 to Brock et al which is incorporated herein in its entirety by reference. The material of Brock et al. is a three layer laminate of spunbonded/meltblown~spunbonded layers, which is also commonly referred to by the acronym "SMS". The two outer layers of SMS are a spunbonded material made from extruded polyolefin fibers laid down in a random pattern and then bonded to one another. The inner layer is a meltblown layer also made from extruded polyolefin fibers generally of a smaller diameter and sometimes having a more discontinuous length than the fibers in the spunbonded layers. As a result, the meltblown layer provides increased barrier properties due to it fine fiber structure which permits the sterilizing agent to pass through the fabric while preventing passage of bacteria and other contaminants. Conversely, the two outer spunbonded layers provide a greater portion of the strength factor in the overall laminate.

Figure 4:
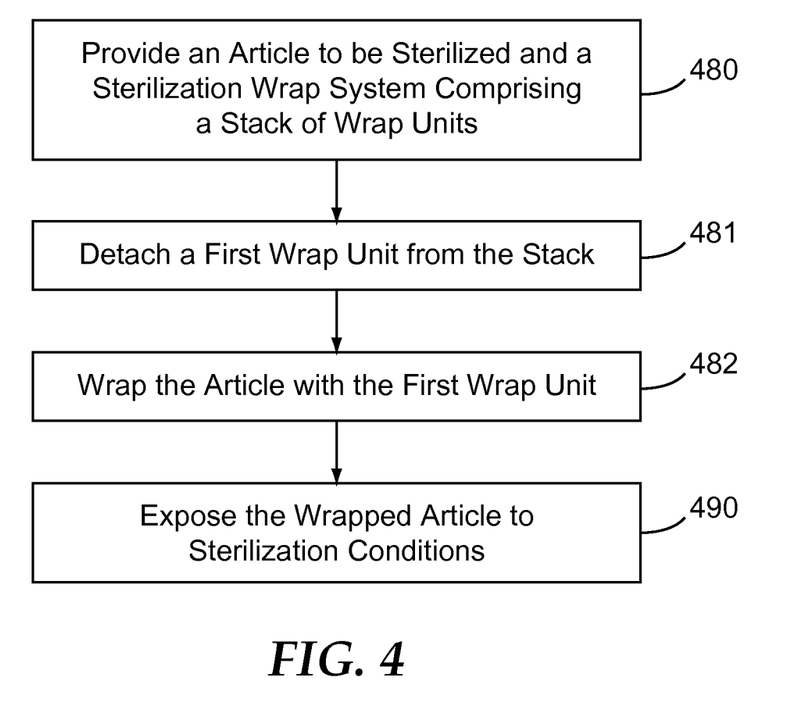
FIG. 4 is a block diagram of one embodiment of a method of sterilizing an article according to the present disclosure.

The present disclosure provides methods for sterilizing an article. FIG. 4 shows a block diagram of one embodiment of a method for sterilizing an article. The method comprises the step 480 of providing an article to be sterilized and a sterilization wrap system that includes a stack of a plurality of wrap units. At least one wrap unit in the stack is detachably attached via an attachment means to at least one other wrap unit, as described herein. Preferably, each wrap unit in the stack is detachably attached via an attachment means to the wrap unit that, if present, is positioned beneath it. The method further includes the step 481 of detaching a first wrap unit from the stack. "Detaching a wrap unit", as used herein refers to physically separating one wrap unit from another wrap unit to which it is detachably attached via an attachment means described herein. The method further includes the step 482 of wrapping the article with the first wrap unit and the step 490 of exposing the wrapped article to sterilization conditions. In some embodiments, detaching the first wrap unit further comprises detaching one or more additional wrap units attached thereto. In these embodiments, wrapping the article with the first wrap unit can further comprise wrapping the article with two or more wrap units. In some embodiments, wrapping the article with two or more wrap units can comprise wrapping the article with two or more wrap units simultaneously. Thus, it is an advantage of these embodiments of the present disclosure that two or more wrap units, coupled to and aligned with each other via an attachment means, can be detached from a stack and used simultaneously to wrap an article for a sterilization with more than one protective layer. In some preferred embodiments of the method, wrapping the article further comprises securing a portion of one wrap unit to another portion of the same wrap unit. This prevents the wrap from unintentionally opening, thereby exposing the article to contamination, after the sterilization process. The portions may be loosely secured by the attachment means coupled to the wrap unit. Preferably, the portions can be firmly secured via another fastener known in the art such as, for example, tape, a clip, a clamp, a rubber binder, string, or the like. Preferably, the means used to secure the portions should not rip, puncture, tear, or otherwise compromise the integrity of the wrap unit in such a way that might allow access of contaminants to the wrapped article after the sterilization process.

In some embodiments of the method, wrapping the article further comprises securing a portion of a first wrap unit to a portion of a second wrap unit. The portions of the first and second wrap units can be secured as described above. Optionally, the fastener further comprises an indicator (e.g., an indicator that indicates exposure to a sterilant such as steam, ethylene oxide, or hydrogen peroxide, for example).

Figure 5:
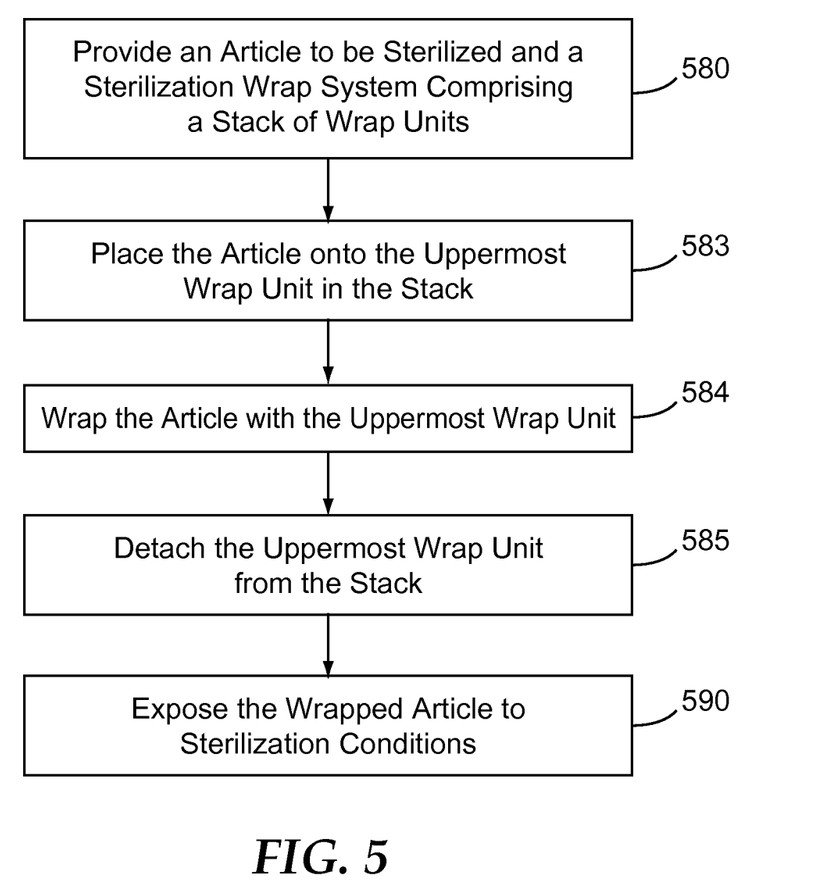
FIG. 5 is a block diagram of another embodiment of a method of sterilizing an article according to the present disclosure.

FIG. 5 shows a bock diagram of another embodiment of a method for sterilizing an article. The method comprises the step 580 of providing an article to be sterilized and a sterilization wrap system that includes a stack of a plurality of wrap units. At least one wrap unit in the stack is detachably attached via an attachment means to at least one other wrap unit, as described herein. Preferably, each wrap unit in the stack is detachably attached via an attachment means to the wrap unit that, if present, is positioned beneath it. The method further includes the step 583 of placing the article onto an uppermost wrap unit in the stack and the step 584 of wrapping the article with the uppermost wrap unit. In these embodiments, wrapping the article with the uppermost wrap unit can further comprise wrapping the article with two or more wrap units (e.g., the uppermost wrap unit and one or more adjacent wrap units). In some embodiments, wrapping the article with two or more wrap units can comprise wrapping the article with two or more wrap units simultaneously. Thus, it is an advantage of these embodiments of the present disclosure that two or more wrap units, coupled to and aligned with each other via an attachment means, can be used simultaneously to wrap an article for sterilization with more than one protective layer. The method further comprises the step 585 of detaching the uppermost wrap unit from the stack. In some embodiments, the uppermost wrap unit may be detached from the stack simultaneously with the wrapping step 584. In some embodiments, detaching the uppermost wrap unit from the stack further comprises detaching two or more wrap units from the stack. In some embodiments of the method, wrapping the article further comprises securing a portion of one wrap unit to another portion of the same wrap unit. The portions can be secured by the attachment means coupled to the wrap unit. Alternatively, the portions can be secured via other fastener known in the art such as, for example, tape, a clip, a clamp, a rubber binder, string, or the like. In some embodiments of the method, wrapping the article further comprises securing a portion of a first wrap unit to a portion of a second wrap unit. The portions of the first and second wrap units can be secured as described above. Optionally, the fastener further comprises an indicator (e.g., an indicator that indicates exposure to a sterilant such as steam, ethylene oxide, or hydrogen peroxide, for example). Referring back to FIG. 5, the method further comprises the step 590 of exposing the wrapped article to sterilization conditions.

Figure 6:
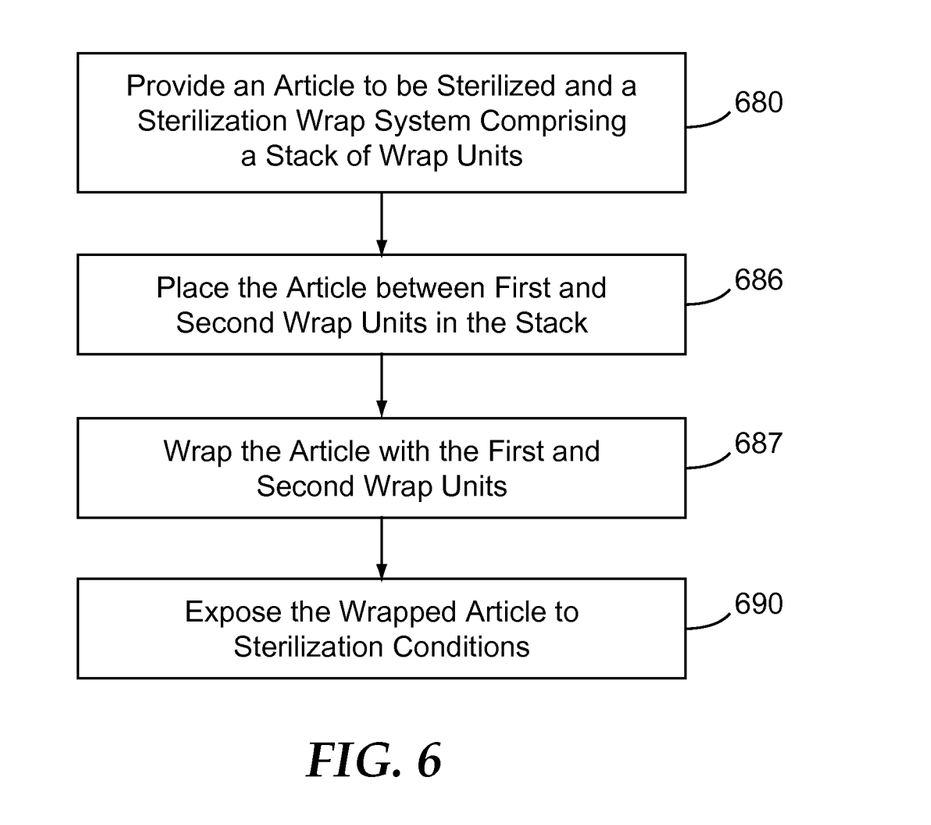
FIG. 6 is a block diagram of another embodiment of a method of sterilizing an article according to the present disclosure.

FIG. 6 shows a bock diagram of another embodiment of a method for sterilizing an article. The method comprises the step 680 of providing an article to be sterilized and a sterilization wrap system that includes a stack of a plurality of wrap units. At least one wrap unit in the stack is detachably attached via an attachment means to at least one other wrap unit, as described herein. Preferably, each wrap unit in the stack is detachably attached via an attachment means to the wrap unit that, if present, is positioned beneath it. The method further comprises the step 686 of placing the article between a first wrap unit and a second wrap unit in the stack. In some embodiments, the first or second wrap unit may be the uppermost wrap unit in the stack. The method further comprises the step 687 of wrapping the article with the first and second wrap units and the step 690 of exposing the wrapped article to sterilization conditions. Optionally, in some embodiments, the first and second wrap units may be detached from the stack prior to placing the article between the wrap units and/or prior to wrapping the article. In some embodiments of the method, wrapping the article further comprises securing a portion of one wrap unit to another portion of the same wrap unit. The portions can be secured by the attachment means coupled to the wrap unit. Alternatively, the portions can be secured via other fastener known in the art such as, for example, tape, a clip, a clamp, a rubber binder, string, or the like. In some embodiments of the method, wrapping the article further comprises securing a portion of a first wrap unit to a portion of a second wrap unit. The portions of the first and second wrap units can be secured as described above. Optionally, the fastener further comprises an indicator (e.g., an indicator that indicates exposure to a sterilant such as steam, ethylene oxide, or hydrogen peroxide, for example).

EMBODIMENTS

Embodiment 1 is a method of sterilizing an article, comprising:
providing an article to be sterilized and a sterilization wrap system that includes a stack of a plurality of wrap units; wherein each wrap unit comprises an upper surface and a lower surface; wherein at least one wrap unit is detachably attached via an attachment means to at least one other wrap unit in the stack;
detaching a first wrap unit from the stack;
wrapping the article with the first wrap unit; and
exposing the wrapped article to sterilization conditions.

Embodiment 2 is a method of sterilizing an article, comprising:
providing an article to be sterilized and a sterilization wrap system that includes a plurality of wrap units configured in a stack; wherein each wrap unit comprises an upper surface and a lower surface; wherein at least one wrap unit is detachably attached via an attachment means to at least one other wrap unit in the stack;
placing the article onto a first wrap unit, wherein the first wrap unit is a topmost wrap unit of the stack;
wrapping the article with the first wrap unit;
detaching the first wrap unit from the stack; and exposing the wrapped article to sterilization conditions.

Embodiment 3 is a method of sterilizing an article, comprising:

providing an article to be sterilized and a sterilization wrap system that includes a plurality of wrap units configured in a stack; wherein each wrap unit comprises an upper surface and a lower surface; wherein at least a first wrap unit is detachably attached via an attachment means to a second wrap unit in the stack;

placing the article between the first and second wrap units, wrapping the article with the first and second wrap units; and exposing the wrapped article to sterilization conditions.

Embodiment 4 is the method of embodiment 1 or embodiment 2, wherein detaching the first wrap unit further comprises detaching the first wrap unit with a second wrap unit attached thereto, wherein wrapping the article comprises wrapping the article with the first and second wrap units.

Embodiment 5 is the method of embodiment 4, wherein wrapping the article comprises simultaneously wrapping the article with the first and second wrap units.

Embodiment 6 is the method of any one of the preceding embodiments, wherein wrapping the article comprises securing a portion of one wrap unit to another portion of the same wrap unit.

Embodiment 7 is the method of embodiment 6, wherein wrapping the article comprises securing a portion of one wrap unit to portion of another wrap unit.

Embodiment 8 is the method of embodiment 6 or embodiment 7, wherein securing a portion comprises securing the portion via the attachment means.

Embodiment 9 is the method of any one of the preceding embodiments, further comprising securing a portion of one wrap unit to another portion of the same wrap unit or securing a portion of one wrap unit to portion of another wrap unit via a fastener.

Embodiment 10 is the method of embodiment 9, wherein the fastener further comprises a visual sterilization indicator.

Embodiment 11 is a sterilization wrap system, comprising:
a plurality of wrap units configured in a stack;
wherein each of the wrap units comprises a sheet material that is substantially permeable to vapor-phase sterilants and has filtration properties sufficient to prevent the passage of pathogenic microorganisms therethrough;
wherein at least one wrap unit is detachably attached via an attachment means to another wrap unit in the stack.

Embodiment 12 is the sterilization wrap system of embodiment 11, wherein the sheet material comprises a nonwoven material or a medical grade paper.

Embodiment 13 is the sterilization wrap system of embodiment 12, wherein the nonwoven material comprises cellulose, rayon, a thermoplastic polymer, a derivative of any of the foregoing materials, or a combination of any two or more of the foregoing materials.

Embodiment 14 is the sterilization wrap of embodiment 13, wherein the thermoplastic polymer comprises a polyolefin polymer, a polyester polymer, or a polyamide polymer.

Embodiment 15 is the sterilization wrap system of any one of embodiments 11 through 14, wherein the sheet material is made using a process selected from the group an air laying process, a wet-laid process, a hydroentangling process, spunbonding, meltblowing, staple fiber carding and bonding, and solution spinning Embodiment 16 is the sterilization wrap system of any one of embodiments 11 through 15, wherein the sterilization wrap consists essentially of a three-ply laminate of spunbond polypropylene-meltblown polypropylene-spunbond polypropylene.

Embodiment 17 is the sterilization wrap system of any one of embodiments 11 through 16, wherein each wrap unit in the stack is detachably attached to a wrap, if present, positioned immediately above it in the stack.

Embodiment 18 is the sterilization wrap system of any one of embodiments 11 through 17, wherein the attachment means is an adhesive means, a mechanical means, or a surface-modification means.

Embodiment 19 is the sterilization wrap system of any one of embodiments 11 through 17, wherein the attachment means comprises a wax.

Embodiment 20 is the sterilization wrap system of any one of embodiments 11 through 19, wherein the attachment means is positioned on a major surface of a first wrap unit, wherein the attachment means is detachably attached to a major surface of a second wrap unit.

Embodiment 21 is the sterilization wrap system of any one of embodiments 11 through 19, wherein the attachment means coupling a first wrap unit to a second wrap unit is positioned along at least a portion of an edge of each of the first and second wrap units.

The present invention is illustrated by the following examples. It is to be understood that the particular examples, materials, amounts, and procedures are to be interpreted broadly in accordance with the scope and spirit of the invention as set forth herein.

EXAMPLES

Example 1

Preparation of a Sterilization Wrap System Using a Double-sided Removable Tape

Figure 7A:
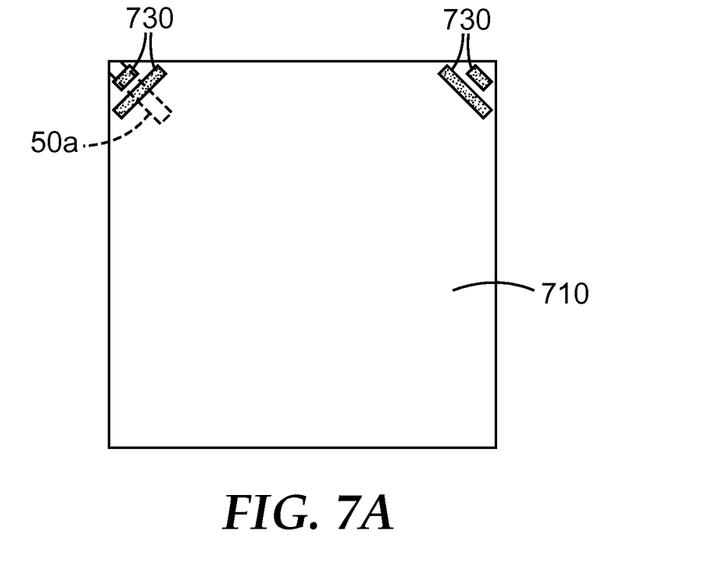
FIG. 7A is a top view of a wrap unit from the sterilization wrap system of FIG. 1, showing the sample described in Example 1.

A stack of sterilization wraps was prepared by placing a 30.5 cm long piece of SCOTCH 667 Double Sided Removable Tape, ¾ inch (1.90 cm) wide, available from 3M Company, St. Paul, Minn., along one edge of a 30.5 cm×30.5 cm (12 inch×12 inch) square cut piece of Kimberly-Clark SPUNGUARD single-ply sterilization wrap (#10712-20 available from Kimberly-Clark, Roswell, Ga.). Another piece of sterilization wrap of the same size was manually pressed onto the tape so that the uppermost new sheet was aligned with the previous sheet. Next, another piece of SCOTCH 667 tape (30.5 cm long) was applied along the same side of the new sheet of sterilization wrap on the same edge. These steps were repeated until a stack of ten sheets was formed. The stack was held together by strips of SCOTCH 667 tape (described above) applied in between each sheet. The strips of tape were all aligned along the same edge of the stack. For each seal strength test replicate, the top two sheets were removed from the stack without being separated from each other. Three replicates were prepared by cutting a 2.54 cm (1 inch) wide by 10 cm (4 inch) long strip of the two sheets joined together with tape. The strips were cut along the edge that included the tape between the sheets. FIG. 7A illustrates a wrap unit 710 constructed according to this Example, showing the position of the tape 730 and the orientation of the cut samples 50*a*. The force needed to separate the individual wrap units was measured using the method described in Example 3.

Example 2

Preparation of a Sterilization Wrap System Using a Double-sided Permanent Tape

Figure 7B:
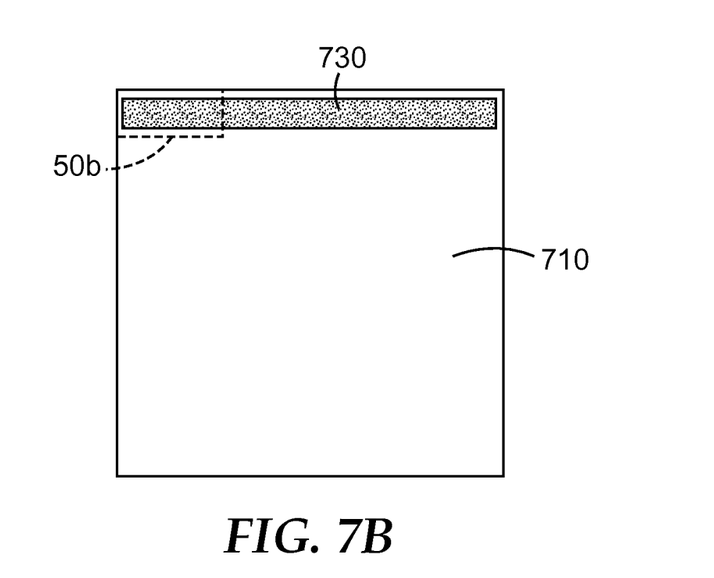
FIG. 7B is a top view of a wrap unit from the sterilization wrap system of FIG. 4, showing the sample described in Example 2.

A stack of sterilization wraps was prepared by using SCOTCH 137 Permanent Double Sided Tape, ½ inch (1.27 cm) wide, available from 3M Company, St. Paul, Minn., applied to 38 cm×38 cm (15 inch×15 inch) square pieces of Kimberly-Clark SPUNGUARD single-ply sterilization wrap (#10715-20 available from Kimberly-Clark, Roswell, Ga.). Two pieces of the double sided tape were applied to each of 2 corners of the wrap sheet. The two pieces of tape, placed in each of 2 corners, were of two different lengths. The first piece of tape was 4.5 cm long and the second piece of tape was 7.5 cm long. The first (4.5 cm) piece of SCOTCH 137 Permanent Double Sided Tape was applied closest to one corner of the sheet in an orientation such that the long axis of the tape was perpendicular to an imaginary line drawn diagonally between opposite corners and the ends of the first piece of tape nearly touched the edges of the sheet. The second (7.5 cm) piece of SCOTCH 137 tape was placed parallel to the first piece of tape separated by about 0.5 cm. FIG. 7B illustrates a wrap unit 710 constructed according to this Example, showing the position of the tape 730 and the orientation of the cut samples 50b. Next, a second piece of sterilization wrap (38 cm×38 cm) was aligned and manually pressed onto the first piece of sterilization wrap, having the tape in the two corners, so that the second sheet was aligned with the first sheet and held to it by the double sided tape positioned in the two corners. Then, additional tape was applied in the same manner to the second sheet of sterilization wrap. These steps were repeated until a stack of ten sheets was formed. For each seal strength test, the top two sheets were removed from the stack without being separated from each other. Two replicates were prepared by cutting a 2.54 cm (1 inch) wide by about 10 cm (4 inch) long strip of the two sheets joined together with tape. For the Type 2 system, the strips were cut in a diagonal direction from one corner with the tape seal towards the center of the sheets. The force needed to separate the individual wrap units was measured using the method described in Example 3.

Example 3

Test of the Force Strength of the Attachment Means of Type 1 and Type 2 Sample

The samples made in Examples 1 and 2 were tested to determine the strength of the attachment between the two sheets. The force necessary to peel apart the adhesive seal between two sheets joined together with double sided tape was measured using a Zwick/Roell Z005 testing machine (available from Zwick/Roell, Ulm, Germany) with a TC-LC0500N (Zwick), load cell. This test simulated the force necessary to separate two sheets of the sterilization wrap pad of two embodiments (Type 1 and Type 2) of the present invention.

The Zwick/Roell Z005 instrument used the testXpert V11.0 software (Zwick) with the following settings: crosshead speed: 130 mm/min; gauge length 6.25 cm.

Figure 8A:
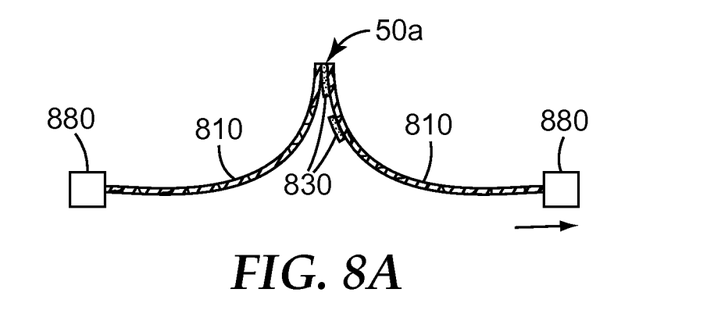
FIG. 8A is a side view of the sample of FIG. 7A, showing the attachment points and direction of the force during testing according to Example 3.
Figure 8B:
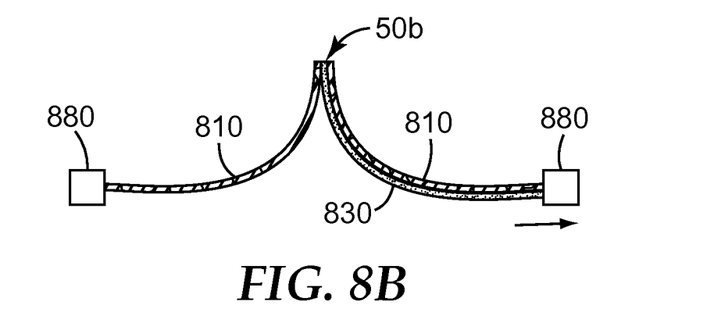
FIG. 8B is a side view of the sample of FIG. 7B, showing the attachment points and direction of the force during testing according to Example 3.

The following procedure was followed. Prior to testing, each cut sample strip was manually pressed with a 2 Kg (4.5 pound) rubber coated roller for 2 seconds. The two sheets of each sample were manually pulled apart just enough to clamp each sheet in one of the two jaws. FIGS. 8A and 8B illustrate the orientation of the wrap units 810, the position of the tape 830, the position of the attachment points 880 for the testing apparatus, and the relative direction (indicated by arrows) of the movement of the crosshead when each of the samples (50a and 50b, respectively) were tested according to this Example. The crosshead was set in motion. The jaws pulled apart the two sheets of each sample replicate, the top jaw pulling upward while the bottom jaw remained stationary. The average force required to separate the two sheets sealed with double sided tape was recorded and is shown in Table 1. The aggregate average force is calculated as the average peel force for all of the samples of each type.

TABLE 1

| Example | Replicate No. | Ave. Force (grams) | Aggregate Ave. Force (g) |
| --- | --- | --- | --- |
| 1 | 1 | 7.0 | 7.5 |
| 1 | 2 | 7.8 | |
| 1 | 3 | 7.7 | |
| 2 | 1 | 55.3 | 51.1 |
| 2 | 2 | 46.9 | |

Various modifications may be made without departing from the spirit and scope of the invention. These and other embodiments are within the scope of the following claims.

The invention claimed is:

1. A sterilization wrap system, comprising:
   a plurality of wrap units configured in a stack;
   wherein each of the wrap units comprises a sheet material that is substantially permeable to vapor-phase sterilants and has filtration properties sufficient to prevent the passage of pathogenic microorganisms therethrough;
   wherein at least one wrap unit is detachably attached via an adhesive means to another wrap unit in the stack.

2. The sterilization wrap system of claim 1, wherein the sheet material comprises medical grade paper or a nonwoven material.

3. The sterilization wrap system of claim 2, wherein the nonwoven material comprises cellulose, rayon, a thermoplastic polymer, a derivative of any of the foregoing materials, or a combination of any two or more of the foregoing materials.

4. The sterilization wrap system of claim 3, wherein the thermoplastic polymer comprises a polyolefin polymer, a polyester polymer, or a polyamide polymer.

5. The sterilization wrap system of claim 1, wherein the sheet material is made using a process selected from the group an air laying process, a wet-laid process, a hydroentangling process, spunbonding, meltblowing, staple fiber carding and bonding, and solution spinning.

6. The sterilization wrap system of claim 1, wherein the sterilization wrap consists essentially of a three-ply laminate of spunbond polypropylene-meltblown polypropylene-spunbond polypropylene.

7. The sterilization wrap system of claim 1, wherein each wrap unit in the stack is detachably attached to a wrap, if present, positioned immediately above it in the stack.

8. The sterilization wrap system of claim 1, wherein the attachment means comprises a wax.

9. The sterilization wrap system of claim 1, wherein the attachment means is positioned on a major surface of a first wrap unit, wherein the attachment means is detachably attached to a major surface of a second wrap unit.

10. The sterilization wrap system of claim 1, wherein the attachment means coupling a first wrap unit to a second wrap unit is positioned along at least a portion of an edge of each of the first and second wrap units.

11. The sterilization wrap system of claim 1, wherein the adhesive means consists of an adhesive layer or an adhesive tape.

* * * * *